US012642990B2

(12) United States Patent
Roeder

(10) Patent No.: US 12,642,990 B2
(45) Date of Patent: Jun. 2, 2026

(54) RADIATION THERAPY ARRANGEMENT AND METHOD FOR OPERATING A RADIATION THERAPY ARRANGEMENT

(71) Applicant: Carl Zeiss Meditec AG, Jena (DE)

(72) Inventor: Norman Roeder, Döbritschen (DE)

(73) Assignee: Carl Zeiss Meditec AG, Jena (DE)

( * ) Notice: Subject to any disclaimer, the term of this patent is extended or adjusted under 35 U.S.C. 154(b) by 191 days.

(21) Appl. No.: 18/243,656

(22) Filed: Sep. 7, 2023

(65) Prior Publication Data

US 2025/0082966 A1     Mar. 13, 2025

(30) Foreign Application Priority Data

Sep. 1, 2022   (DE) ..................... 10 2022 209 110.8

(51) Int. Cl.
*A61N 5/10* (2006.01)
(52) U.S. Cl.
CPC ......... *A61N 5/1048* (2013.01); *A61N 5/1077* (2013.01)
(58) Field of Classification Search
None
See application file for complete search history.

(56) References Cited

U.S. PATENT DOCUMENTS

| | | | |
|---|---|---|---|
| 10,549,122 B2 * | 2/2020 | Cheng | A61N 5/1069 |
| 2004/0260142 A1 | 12/2004 | Lovoi | |
| 2008/0242969 A1 * | 10/2008 | Sayeh | A61B 6/466 |
| | | | 600/407 |

| | | | |
|---|---|---|---|
| 2013/0064346 A1 * | 3/2013 | Ferren | A61B 6/51 |
| | | | 378/62 |
| 2014/0051904 A1 | 2/2014 | Solf et al. | |
| 2015/0035942 A1 * | 2/2015 | Hampton | A61N 5/1049 |
| | | | 348/42 |
| 2016/0029981 A1 | 2/2016 | Van Dijk et al. | |
| 2017/0239491 A1 | 8/2017 | Xia et al. | |

(Continued)

FOREIGN PATENT DOCUMENTS

| | | |
|---|---|---|
| DE | 102020200400 A1 | 8/2020 |

OTHER PUBLICATIONS

Office Action issued in German Patent Application No. DE 10 2022 209 110.8, dated Nov. 15, 2022 (to which this application claims priority), and English language translation thereof.

(Continued)

*Primary Examiner* — Marcus H Taningco
(74) *Attorney, Agent, or Firm* — Ewers IP Law PLLC; Falk Ewers

(57) ABSTRACT

A radiation therapy arrangement includes a holding device, an x-ray source, on which an applicator can be arranged, wherein the x-ray source is arranged on the holding device and is held with the holding device so as to be positionable and orientable, a sensor system, which is configured to capture a pose and/or a pose change of the x-ray source and/or of the applicator at least during radiation, and a control device, wherein the control device is configured to evaluate the captured pose and/or the captured pose change and, proceeding from the captured pose and/or the captured and/or a determined pose change, to perform or initiate a shut-off of the x-ray source. Furthermore, the disclosure relates to a method for operating a radiation therapy arrangement.

10 Claims, 1 Drawing Sheet

(56)                    References Cited

U.S. PATENT DOCUMENTS

2020/0038691  A1      2/2020  Fishman et al.
2025/0082504  A1*     3/2025  Donitzky .............. A61F 9/0084

OTHER PUBLICATIONS

"Zeiss-Intrabeam 600", Carl Zeiss Meditec AG Brochure, Carl Zeiss Meditec AG, Jena, Germany, (2020).
Office Action issued in German Patent Application No. DE 10 2022 209 110.8, dated Dec. 19, 2025 (from which this application claims priority) and English language translation thereof.

* cited by examiner

RADIATION THERAPY ARRANGEMENT AND METHOD FOR OPERATING A RADIATION THERAPY ARRANGEMENT

CROSS REFERENCE TO RELATED APPLICATIONS

This application claims priority to German patent application DE 10 2022 209 110.8, filed Sep. 1, 2022, the entire content of which is incorporated herein by reference.

TECHNICAL FIELD

The disclosure relates to a radiation therapy arrangement and to a method for operating a radiation therapy arrangement.

BACKGROUND

In intraoperative radiation therapy or radio therapy (IORT), what are known as applicators are used during tumor bed radiation (e.g., in the INTRABEAM system by Carl Zeiss Meditec AG). The applicators allow access to the radiation site in the body of the patient. The applicators absorb some of the x-ray radiation and can in this way influence the radiation. This influence must be taken into account during radiation planning. The relevant applicator data (e.g., depth-dose curve) are generally stored on a computer for radiation planning.

Each applicator allows the introduction of a miniaturized movable x-ray source such that an isocenter of the x-ray source is located, as the origin of the x-ray radiation, at a defined position (e.g., in a sphere center of the applicator). Open-loop and/or closed-loop control of the x-ray source is generally effected from a control panel. Part of the control panel is formed by the control unit of the x-ray source, which is connected to the x-ray source via a supply and control line. It is typical during radiation that a holding device of the x-ray source and of the applicator that is arranged thereon is located in an operating theater or a treatment room, but the control panel is operated from outside it.

The applicator and the x-ray source form a unit over the radiation period and are held in position by the holding device during the radiation. Such a holding device can be, for example, a stand having a plurality of movement axes or degrees of freedom. In the normal case, the operator, e.g., a surgeon or an assistant, moves the applicator into the tumor cavity with the aid of the holding device, wherein the applicator is then held in the respective desired position during radiation by the holding device.

As a consequence of normative requirements, shut-off apparatuses of x-ray sources must be configured to be first-fault safe, i.e., safe operation must be possible even when a fault occurs. This can be achieved, for example, by virtue of the fact that all necessary radiation parameters are present in the control unit of the x-ray source from the start of a radiation treatment, which means that radiation can be completed in a controlled manner even if the control panel fails. For example, the failure of the computing unit of the control panel would therefore not automatically stop the radiation. Furthermore, it is known to hard-wire a "door switch" directly to the control unit of the x-ray source. If someone enters the room in which the radiation is currently taking place, the "door switch" is actuated when the door is opened and the x-ray source is automatically shut off immediately.

SUMMARY

It is an object of the disclosure to improve a radiation therapy arrangement and a method for operating a radiation therapy arrangement, in particular regarding operational safety.

According to an aspect of the disclosure, the object is achieved by a radiation therapy arrangement and by a method for operating a radiation therapy arrangement as described herein.

It is one of the core concepts of the disclosure to capture a pose and/or a pose change of the x-ray source and/or of an applicator arranged thereon during radiation. This is accomplished with a sensor system which is configured for this purpose. The captured pose and/or the captured pose change is evaluated with a control device, which is connected to the sensor system for the exchange of signals. Shut-off of the x-ray source is performed or initiated with the control device proceeding from the captured pose and/or the captured and/or a determined pose change. Provision may be made here for the pose change to be determined from the captured pose with the control device, for example by calculating the difference between individual values of the captured pose. The background of this procedure is that the x-ray radiation during radiation therapy is very low-energy compared to linear accelerators and therefore has a very strongly decreasing depth-dose curve. This results in even very small position deviations during radiation having a large effect on the dose distribution applied in the radiated tissue. To avoid radiation of healthy tissue, a pose and/or a pose change of the x-ray source and/or of the applicator can be monitored with the radiation therapy arrangement described in this disclosure and with the method, and, proceeding from the pose and/or the pose change, measures for shutting off the x-ray source can be taken.

The radiation therapy arrangement and the method improve safety during the radiation because it is possible to monitor a pose and/or a pose change. Undesirable and harmful radiation of healthy tissue can be prevented in this way.

In particular, a radiation therapy arrangement is created including a holding device and an x-ray source, on which an applicator can be arranged, wherein the x-ray source is arranged on the holding device and is held with the holding device so as to be positionable and orientable, and a sensor system, which is configured to capture a pose and/or a pose change of the x-ray source and/or of the applicator at least during radiation, and a control device, wherein the control device is configured to evaluate the captured pose and/or the captured pose change and, proceeding from the captured pose and/or the captured and/or a determined pose change, to perform or initiate a shut-off of the x-ray source.

Furthermore provided is in particular a method for operating a radiation therapy arrangement, wherein a pose and/or a pose change of an x-ray source arranged on a holding device and/or of an applicator arranged on the x-ray source is captured at least during radiation with a sensor system, wherein the captured pose and/or the captured pose change is evaluated with the control device, and wherein, proceeding from the captured pose and/or the captured and/or a determined pose change, a shut-off of the x-ray source is performed or initiated with the control device.

Parts of the control device can be embodied, either individually or together, as a combination of hardware and software, for example as program code that is executed on a microcontroller or microprocessor. However, provision can also be made for parts to be configured as applicationspecific integrated circuits (ASICs) and/or field-programmable gate arrays (FPGAs), either on their own or in combination.

The holding device can in particular be a stand. In particular, the stand can be a multi-jointed stand which can be moved around multiple axes or can provide a plurality of degrees of freedom for the x-ray source and the applicator arranged thereon. In particular, the stand can be a 6-axis stand. The stand is in particular mechanically supported and/or supported by motor, for example with the aid of servomotors.

A sensor system can include one or more sensors. The sensors can be of the same type or of different types. The sensors can be in particular position sensors and/or angle sensors (e.g., on rotational axes). The sensors can be potentiometers, for example. For example, an angular position can be determined depending on voltage values of the potentiometer.

Provision may be made for the sensor system to include an optical sensor system. Provision can be made, for example, for the pose and/or the pose change to be captured with the aid of optical markers arranged on the holding device and/or on the x-ray source and/or on the applicator and of at least one camera.

In one embodiment, provision is made for the control device to be furthermore configured to compare the captured and/or determined pose change with a specified threshold value and to perform or initiate the shut-off if a comparison result shows that the captured and/or determined pose change is larger than the specified threshold value. A threshold value for a maximum pose change can be specified hereby which should be observed during radiation. If the value for the maximum pose change is exceeded, the radiation is terminated by shutting off the x-ray source.

In one exemplary embodiment, provision is made for the sensor system to be arranged in and/or on the holding device. In this way, an x-ray source and an applicator can continue to be operated as they have been so far, without further extensions or attachments thereon being necessary. For example, provision may be made for one or more position sensors and/or angle sensors to be arranged in and/or on the holding device in order to capture a movement of the holding device and, moreover, to determine or estimate a pose and/or a pose change of the x-ray source and/or of the applicator. The sensor system captures a position and/or angle etc. at the holding device. The pose and/or pose change of the x-ray source and/or of the applicator can be determined and/or estimated via a mechanically fixed relationship with the x-ray source arranged on the holding device and with the applicator arranged on the x-ray source. For example, a mathematical transformation of positions and/or angles or position changes and/or angle changes of the holding device or of parts of the holding device into a pose and/or pose change of the x-ray source and/or of the applicator can be determined and/or used to this end.

In one exemplary embodiment, provision is made for the radiation therapy arrangement to comprise an interruption switch which is or can be incorporated in a signal chain of a safety door switch, wherein the control device is furthermore configured to control the interruption switch for shutting off the x-ray source. An existing system can be extended easily hereby, without the need to change pre-existing control and monitoring processes. For example, provision may be made for the interruption switch to be introduced or integrated into a signal link with the safety door switch. In this way it is possible in particular to continue to use an existing infrastructure. The control and monitoring functions and devices which cause a shut-off of the x-ray source when the door is opened can thus continue to be used. The interruption switch has in particular an "actively on" functionality (or a "normally off" characteristic), which is to say that the interruption switch must be actively closed, for example using a control voltage that is intended herefor and is provided by the control device. If this control voltage is missing, for example because a pose change has been detected or because a voltage supply of the control device has failed, the interruption switch is opened automatically and a signal chain of the safety door switch is interrupted, which causes the x-ray source to be shut off.

In one exemplary embodiment, provision is made for the radiation therapy arrangement to comprise an optical interlock system, which can be used to detect and check for the presence of an applicator on the x-ray source, wherein the optical interlock system is configured such that a position and/or a property of at least one mirror in the optical signal path can be changed in a controlled manner such that the optical signal path is interrupted, wherein the control device is furthermore configured to control the at least one mirror for shutting off the x-ray source such that the optical signal path is interrupted. An existing optical interlock system in particular can be extended easily hereby, without the need to change control and monitoring processes. For example, provision may be made for the at least one mirror to be introduced or integrated into a pre-existing optical interlock system. In this way it is possible in particular to continue to use an existing infrastructure. In an optical interlock system, a light beam is typically deflected multiple times in order to travel from a light source, for example a light-emitting diode or a laser diode, to a photodetector, for example a photodiode. If light is captured with the photodetector, the interlock system is closed, and operation of the x-ray source is enabled. By contrast, if no light is captured with the photodetector, the interlock system does not enable operation of the x-ray source. The exemplary embodiment utilizes this fact by introducing the at least one mirror into the signal path of the light at a suitable position, resulting in the light being deflected in a suitable manner such that it travels from the light source to the photodetector or in order to interrupt the signal path by changing the position and/or the property of the mirror.

An exemplary embodiment makes provision for the optical interlock system to be configured such that an angular position of at least one partial area of the at least one mirror can be changed in a controlled manner in order to interrupt the optical signal path. The angular position can be controlled both by motor and also magnetically. In particular, the at least one mirror is moved out, in particular folded out, of the signal path, which interrupts the signal path. A light beam used for the interlock system then no longer reaches the photodetector.

A further exemplary embodiment makes provision for the optical interlock system to be configured such that a reflectance of the at least one mirror can be changed in a controlled manner in order to interrupt the optical signal path. For example, the at least one mirror can include micro-mirrors with which a reflection angle can be set in a controlled manner. For example, the at least one mirror can include a micro-mirror actuator (digital micromirror device, DMD, for example by Texas Instruments, USA). However, provision may also be made for a liquid crystal layer (e.g., a liquid crystal display, LCD) to be arranged on a mirror surface, which liquid crystal layer can change a degree of transmission in a controlled manner such that a reflectance at the at least one mirror can be changed thereby in order to interrupt the signal path.

In one exemplary embodiment, provision is made for the radiation therapy arrangement to include a communication link to an operating apparatus with which the radiation therapy arrangement can be operated, wherein the control device is configured to transmit the captured pose and/or the captured and/or determined pose change and/or a shut-off signal to the operating apparatus via the communication link. In this way, it is possible to provide a user of the radiation therapy arrangement with information and/or feedback relating to the captured pose and/or to the determined and/or captured pose change on the operating apparatus. Furthermore, a controlled shut-off can also take place via the operating apparatus which typically provides power to the x-ray source. Provision may furthermore be made for recording of the pose and/or of the pose change to be initiated with the operating apparatus. The communication link may be configured in wired or wireless form.

Furthermore, a radiation therapy system is also provided, including an operating apparatus and a radiation therapy arrangement in accordance with any of the described exemplary embodiments.

Further features relating to the configuration of the method are evident from the description of configurations of the radiation therapy arrangement. Here, the advantages of the method are respectively the same as in the configurations of the radiation therapy arrangement.

BRIEF DESCRIPTION OF THE DRAWINGS

The disclosure will now be described with reference to the drawings wherein.

DESCRIPTION OF EXEMPLARY EMBODIMENTS

Figures 1, 2:
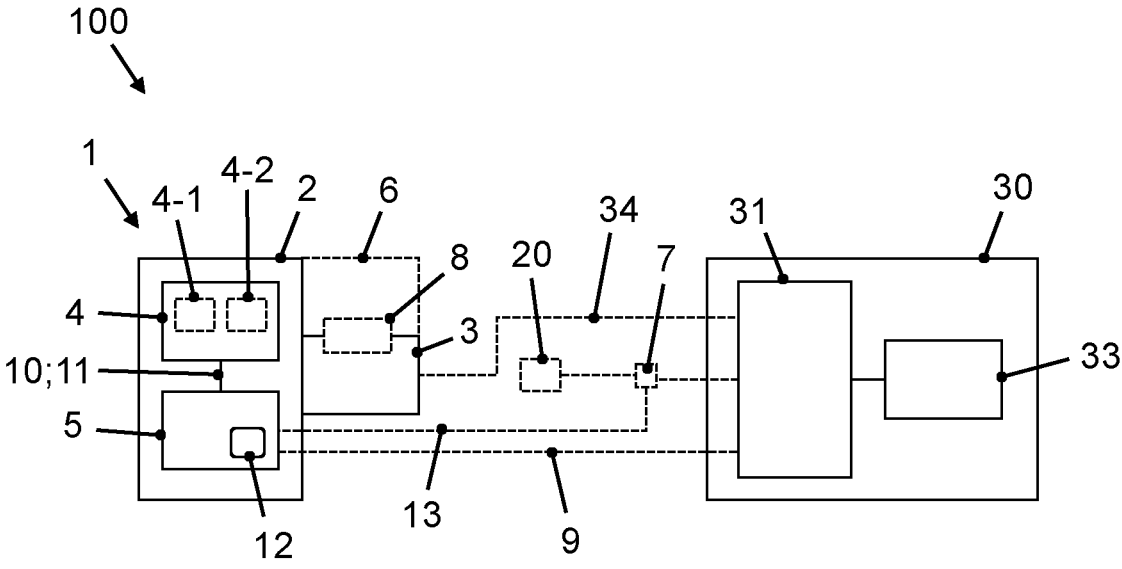
FIG. 1 shows a schematic illustration of exemplary embodiments of the radiation therapy arrangement and of the radiation therapy system.
FIG. 2 shows a schematic illustration for elucidating a further exemplary embodiment of the radiation therapy arrangement.

FIG. 1 shows a schematic illustration of one exemplary embodiment of the radiation therapy arrangement 1. The radiation therapy arrangement 1 includes a holding device 2, an x-ray source 3, a sensor system 4, and a control device 5. The holding device 2 is configured for example as a multi-jointed stand having multiple degrees of freedom. The x-ray source 3 is arranged on the holding device 2 and can be positioned and oriented in the degrees of freedom with the holding device 2. An applicator 6 can be arranged on the x-ray source 3. When the applicator 6 is arranged on the x-ray source 3, the applicator can be arranged, together with the x-ray source 3, in a tumor cavity of a patient for radiation purposes with the holding device 2, in particular with the stand, and can be held there in a specified position and orientation (pose). The applicator 6 is in particular interchangeable and can be selected specifically for the respective radiation task (e.g., surface radiation, radiation of a tumor cavity with isotropic distribution of the radiation dose etc.).

The sensor system 4 is configured to capture a pose 10 and/or a pose change 11 of the x-ray source 3 and/or of the applicator 6 at least during radiation. In particular, the sensor system 4 is arranged in and/or on the holding device 2 and captures a pose and/or a pose change of the holding device 2, which can then be converted by calculation into a pose 10 and/or a pose change 11 of the x-ray source 3 and/or of the applicator 6 by way of a transformation rule. The conversion can take place with the sensor system 4 or in the control device 5. The sensor system 4 can include for example position sensors 4-1 and/or angle sensors 4-2 with which the pose and/or the pose change of the holding device 2 can be captured, in particular by capturing axis positions.

The control device 5 includes, for example, a computing device and a memory (neither of which is shown) in order to enable calculation operations. The control device 5 is configured to evaluate the captured pose 10 and/or the captured pose change 11 and, proceeding from the captured pose 10 and/or the captured and/or a determined pose change 11, to perform or initiate a shut-off of the x-ray source 3. Provision may be made here for the control device 5 to determine the pose change 11 from the captured pose 10, for example by calculating the corresponding difference between captured poses 10 over the radiation period.

Together with an operating apparatus 30, the radiation therapy arrangement 1 forms a radiation therapy system 100. The operating apparatus 30 includes a control unit 31 for the x-ray source 3, which also supplies power to the x-ray source 3. The control unit 31 and the x-ray source 3 are connected to one another for this purpose via a supply and control line 34. The operating apparatus 30 furthermore includes a display and operating device 33 for displaying information and for operating the radiation therapy system 100.

In particular, provision may be made for the radiation therapy arrangement 1 to include a communication link 9 to the operating apparatus 30, wherein the control device 5 is configured to transmit the captured pose 10 and/or the captured and/or determined pose change 11 and/or a shut-off signal to the operating apparatus 30 via the communication link 9. The pose 10 and/or the pose change 11 can be displayed on the display and operating device 33 for information purposes, for example. The shut-off signal, by contrast, serves to allow the x-ray source 3 to be shut off via the control unit 31, for example by interrupting the power supply to the x-ray source 3.

Provision may be made for the control device 5 to furthermore be configured to compare the captured and/or determined pose change 11 with a specified threshold value 12 and to perform or initiate the shut-off if a comparison result shows that the captured and/or determined pose change 11 is larger than the specified threshold value 12. Such a threshold value 12 is in particular a specification for a maximum position change of the x-ray source 3 and/or of the applicator 6 arranged thereon during the radiation. Such a threshold value 12 can be, for example, a specification of a position change in a dimension of at most +/−1 mm. The pose 10 and/or pose change 11 are constantly compared with the specified threshold value 12 during the radiation and, as soon as the specified threshold value 12 has been reached or exceeded, the shut-off is performed or initiated. The threshold value 12 can be specified, for example, with the aid of the operating apparatus 30 and is stored in the memory of the control device 5, for example.

Provision may be made for the radiation therapy arrangement 1 to include an interruption switch 7 which is or can be incorporated in a signal chain of a safety door switch 20, wherein the control device 5 is furthermore configured to control the interruption switch 7 for shutting off the x-ray source 3. The safety door switch 20 ensures that the x-ray source 3 is shut off if a door leading to the treatment room is opened during radiation. By incorporating the interruption switch 7 into the signal chain of the safety door switch 20, the function of the safety door switch 20 can be utilized to shut off the x-ray source 3. The interruption switch 7 has in particular an "actively closed" characteristic (or a "normally off" characteristic), which is to say a closed state must be brought about actively by way of a control voltage. If this control voltage is missing, the interruption switch 7 opens. The control device 5 is connected to the interruption switch 7 via a control line 13.

Provision may be made for the radiation therapy arrangement 1 to include an optical interlock system 8, which can be used to detect and check for the presence of an applicator 6 on the x-ray source 3, wherein the optical interlock system 8 is configured such that a position and/or a property of at least one mirror in the optical signal path can be changed in a controlled manner so that the optical signal path is interrupted.

This is schematically illustrated for one exemplary embodiment in FIG. 2. The optical interlock system 8 includes a light source 8-1, for example a light-emitting diode or laser diode, a photodetector 8-2, for example a photodiode, on the side of the x-ray source 3, and two mirrors 8-3, 8-4 on the side of the applicator 6. The optical interlock system 8 furthermore includes in particular a controllable mirror 8-5 on the side of the x-ray source 3. A position of the controllable mirror 8-5 can be brought in a controlled manner into two angular positions 16-1, 16-2. Hereby, the optical signal path 15 can be deliberately interrupted. Provision may be made for the controllable mirror 8-5 to be preloaded in one of the angular positions 16-1, 16-2, in particular in the angular position 16-1, with a spring. In the normal case, the optical interlock system 8 monitors for the presence of an applicator 6 on the x-ray source 3. If an applicator 6 is present and arranged correctly on the x-ray source 3, light from the light source 8-1 can travel via the signal path 15 to the photodetector 8-2 and the presence of the applicator 6 can be captured thereby. If no applicator 6 is arranged on the x-ray source 3, the light does not travel from the light source 8-1 to the photodetector 8-2, and it is possible thereby to detect the absence of the applicator 6. The signal path 15 can also be interrupted in a controlled manner by the controllable mirror 8-5 if the applicator 6 is present and operation of the x-ray source 3 can be stopped thereby. A signal from the optical interlock system 8 is transmitted to the operating device 30 (FIG. 1) via the supply and control line 34 (FIG. 1).

The control device 5 is configured to control the controllable mirror 8-5 for shutting off the x-ray source 3 such that the optical signal path 15 is or has been interrupted. Shutting off the x-ray source 3 is then effected via the operating apparatus 30, using the same functionality that stops the operation of the x-ray source 3 if the applicator 6 is missing.

As an alternative to a single large controllable mirror 8-5 with only one single mirror area, it is also possible to use a micromirror actuator (not shown, digital micromirror device, DMD), in which a plurality of mirror elements, arranged in a two-dimensional grid, can be controlled such that an angle at which light that is incident on the mirror elements is reflected is redirected into a direction which is specified in a controlled manner. The control device 5 then controls the micromirror actuator accordingly.

As an alternative or in addition, provision may be made for the optical interlock system 8 to be configured such that a reflectance of the controllable mirror 8-5 can be changed in a controlled manner in order to interrupt the optical signal path 15. For example, provision may be made for a liquid crystal to be arranged in front of the mirror 8-5 (in which then an angular position in particular cannot be changed), in which liquid crystal a degree of transmission can be controlled and a reflectance at the mirror 8-5 can be controlled thereby. The control device 5 then controls the liquid crystal accordingly.

LIST OF REFERENCE NUMERALS

1 Radiation therapy arrangement
2 Holding device
3 X-ray source
4 Sensor system
4-1 Position sensor(s)
4-2 Angle sensor(s)
5 Control device
6 Applicator
7 Interruption switch
8 Optical interlock system
8-1 Light source
8-2 Photodetector
8-3 Mirror
8-4 Mirror
8-5 Controllable mirror
9 Communication link
10 Pose
11 Pose change
12 Threshold value
15 Optical signal path
16-1 Angular position (closed signal path)
16-2 Angular position (interrupted signal path)
20 Safety door switch
30 Operating apparatus
31 Control unit
33 Display and operating device
34 Supply and control line
100 Radiation therapy system

What is claimed is:

1. A radiation therapy arrangement, comprising:
a holding device;
an x-ray source, on which an applicator can be arranged, wherein, when an irradiation mode is activated, the applicator is positioned in or in contact with a patient, and wherein the x-ray source is arranged on the holding device and is held with the holding device so as to be positionable and orientable;
a sensor system configured to capture a pose and/or a pose change of the x-ray source and/or of the applicator during radiation;
a control device configured to evaluate the captured pose and/or the captured pose change and, proceeding from the captured pose and/or the captured and/or a determined pose change, to perform or initiate a shut-off of the x-ray source; and
an optical interlock system configured to detect and check for the presence of the applicator on the x-ray source, wherein the optical interlock system includes an optical component arranged in the optical signal path, and wherein the optical interlock system is configured such that the optical component in the optical signal path can be controlled such that the optical component interrupts the optical signal path.

2. The radiation therapy arrangement as claimed in claim 1, wherein the control device is further configured to compare the captured and/or determined pose change with a specified threshold value and to perform or initiate the shut-off when a comparison result shows that the captured and/or determined pose change is larger than the specified threshold value.

3. The radiation therapy arrangement as claimed in claim 1, wherein the sensor system is arranged in and/or on the holding device.

4. The radiation therapy arrangement as claimed in claim 1, further comprising an interruption switch, which is or can be incorporated in a signal chain of a safety door switch, and wherein the control device is furthermore configured to control the interruption switch for shutting off the x-ray source.

5. The radiation therapy arrangement as claimed in claim 1, wherein the optical component is at least one mirror, wherein the optical interlock system is further configured such that a position and/or a property of the at least one mirror in the optical signal path can be changed in a controlled manner such that the optical signal path is interrupted, and wherein the control device is furthermore configured to control the at least one mirror for shutting off the x-ray source such that the optical signal path is interrupted.

6. The radiation therapy arrangement as claimed in claim 5, wherein the optical interlock system is configured such that an angular position of at least one partial area of the at least one mirror can be changed in a controlled manner in order to interrupt the optical signal path.

7. The radiation therapy arrangement as claimed in claim 5, wherein the optical interlock system is configured such that a reflectance of the at least one mirror can be changed in a controlled manner in order to interrupt the optical signal path.

8. The radiation therapy arrangement as claimed in claim 1, further comprising a communication link to an operating apparatus with which the radiation therapy arrangement can be operated, wherein the control device is configured to transmit at least one of the captured pose, the captured and/or determined pose change, and a shut-off signal to the operating apparatus via the communication link.

9. A radiation therapy system comprising:

an operating apparatus; and a radiation therapy arrangement as claimed in claim 1.

10. A method for operating a radiation therapy arrangement, the method comprising:

capturing at least one of a pose and a pose change of an x-ray source arranged on a holding device and/or of an applicator arranged on the x-ray source is captured with a sensor system at least during radiation; and detecting and checking for, with an optical interlock system, the presence of the applicator on the x-ray source, wherein the optical interlock system includes an optical component arranged in the optical signal path, wherein the optical interlock system is configured such that the optical component in the optical signal path can be controlled such that the optical component interrupts the optical signal path, wherein, when an irradiation mode is activated, the applicator is positioned in or in contact with a patient, wherein the at least one of the captured pose and the captured pose change is evaluated with a control device, and wherein a shut-off of the x-ray source is performed or initiated with the control device proceeding from the captured pose and/or the captured and/or a determined pose change.

\* \* \* \* \*